(12) United States Patent
Kamishita et al.

(10) Patent No.: US 11,020,346 B2
(45) Date of Patent: Jun. 1, 2021

(54) RHINAL SPRAY NOZZLE USED FOR MEDICAL SYRINGE

(71) Applicant: TOKO YAKUHIN KOGYO KABUSHIKI KAISHA, Osaka (JP)

(72) Inventors: Taizou Kamishita, Osaka (JP); Takashi Miyazaki, Osaka (JP); Shinya Hoshino, Tokyo (JP)

(73) Assignee: TOKO YAKUHIN KOGYO KABUSHIKI KAISHA, Osaka (JP)

( * ) Notice: Subject to any disclaimer, the term of this patent is extended or adjusted under 35 U.S.C. 154(b) by 747 days.

(21) Appl. No.: 15/322,011

(22) PCT Filed: Jun. 24, 2015

(86) PCT No.: PCT/JP2015/068199
§ 371 (c)(1),
(2) Date: Dec. 23, 2016

(87) PCT Pub. No.: WO2015/199130
PCT Pub. Date: Dec. 30, 2015

(65) Prior Publication Data
US 2017/0128364 A1     May 11, 2017

(30) Foreign Application Priority Data

Jun. 25, 2014  (JP) .............................. JP2014-130150

(51) Int. Cl.
*A61M 15/08*   (2006.01)
*A61K 9/12*    (2006.01)
(Continued)

(52) U.S. Cl.
CPC .............. *A61K 9/12* (2013.01); *A61K 39/145* (2013.01); *A61K 47/02* (2013.01); *A61K 47/10* (2013.01);
(Continued)

(58) Field of Classification Search
CPC .... A61M 11/00; A61M 11/007; A61M 15/08; A61M 2206/16; A61M 2210/0618
See application file for complete search history.

(56) References Cited

U.S. PATENT DOCUMENTS 3,669,359 A * 6/1972 Focht .................... B05B 1/3436
                                                    239/491
5,064,122 A    11/1991 Kamishita et al.
(Continued)

FOREIGN PATENT DOCUMENTS

EP    0499690         8/1992
EP    0526824 A2      2/1993
(Continued)

OTHER PUBLICATIONS

U.S. Appl. No. 15/322,001, filed Dec. 23, 2016.
(Continued)

*Primary Examiner* — Timothy A Stanis
(74) *Attorney, Agent, or Firm* — Hamre, Schumann, Mueller & Larson, P.C.

(57) ABSTRACT

The present invention has a purpose to achieve desired spray characteristics when a pharmaceutical formulation is sprayed by means of a rhinal spray nozzle used for a metered-dose syringe-based squirt.
The present invention relates to a rhinal spray nozzle used for a medical syringe having a tip opening in fluid communication with a syringe barrel for storing a pharmaceutical formulation. The rhinal spray nozzle comprises a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the formulation comprises the gel material containing viscosity modification agent and carboxy vinyl polymer of which viscosity is
(Continued)

modified by applying an exogenous shear force, and wherein the nozzle orifice has a diameter in a range between 0.25 mm and 0.30 mm.

9 Claims, 15 Drawing Sheets

(51) Int. Cl.
    *A61K 47/02*      (2006.01)
    *A61K 47/32*      (2006.01)
    *B05B 1/34*      (2006.01)
    *A61M 11/00*      (2006.01)
    *A61K 39/145*      (2006.01)
    *A61K 47/10*      (2017.01)
    *C12N 7/00*      (2006.01)
    *A61K 39/00*      (2006.01)

(52) U.S. Cl.
    CPC ............ *A61K 47/32* (2013.01); *A61M 11/00* (2013.01); *A61M 11/007* (2014.02); *A61M 15/08* (2013.01); *B05B 1/34* (2013.01); *C12N 7/00* (2013.01); *A61K 2039/5252* (2013.01); *A61K 2039/543* (2013.01); *A61K 2039/55505* (2013.01); *A61K 2039/55511* (2013.01); *A61M 2206/16* (2013.01); *A61M 2210/0618* (2013.01); *C12N 2760/16034* (2013.01)

(56) References Cited

U.S. PATENT DOCUMENTS

| | | | |
|---|---|---|---|
| 5,215,739 | A | 6/1993 | Kamishita |
| 6,443,370 | B1 | 9/2002 | Brulle et al. |
| 8,347,879 | B2 | 1/2013 | Davies et al. |
| 2009/0275668 | A1 | 11/2009 | Kamishita |
| 2010/0308082 | A1 | 12/2010 | Lamble et al. |
| 2012/0082697 | A1 | 4/2012 | Hasegawa et al. |
| 2012/0205464 | A1* | 8/2012 | Pardonge .......... A61M 15/0085 239/102.1 |
| 2015/0075520 | A1 | 3/2015 | Kakuta et al. |
| 2016/0015800 | A1 | 1/2016 | Hasegawa et al. |

FOREIGN PATENT DOCUMENTS

| | | |
|---|---|---|
| EP | 0412524 B1 | 3/1993 |
| EP | 1092447 | 4/2001 |
| JP | H02-91553 | 7/1990 |
| JP | H0291553 U | 7/1990 |
| JP | H03-38529 | 2/1991 |
| JP | H03198866 | 8/1991 |
| JP | H03198866 A | 8/1991 |
| JP | H03-114248 | 11/1991 |
| JP | 2002509026 | 3/2002 |
| JP | 2012521965 | 9/2012 |
| JP | 5185109 | 1/2013 |
| JP | 2014091064 | 5/2014 |
| WO | 2007123193 | 11/2007 |
| WO | 2010114169 | 10/2010 |
| WO | 2013145789 | 10/2013 |
| WO | 2014103488 A1 | 7/2014 |

OTHER PUBLICATIONS

The extended European search report issued in EP15811100.5 dated Feb. 6, 2018, 7 pages.
International Search Report of International Application No. PCT/JP2015/068199, dated Sep. 8, 2015, total 3 pages.
International Search Report of International Application No. PCT/JP2015/068198, dated Sep. 15, 2015, total 2 pages.
Birkhoff, M. et al., "Advantages of Intranasal Vaccination and Considerations on Device Selection", Indian Journal of Pharmaceutical Sciences, 2009, p. 729-731.
Oka et al., "Influenza vaccine: enhancement of immune response by application of carboxy-vinylpolymer", Vaccine, vol. 8, Dec. 1990, p. 573-576, 4 pages.
Ainai et al., "Intranasal vaccination with an inactivated whole influenza virus vaccine induces strong antibody responses in serum and nasal mucus of healthy adults", Human Vaccines & Immunotherapeutics, vol. 9, Issue 9, p. 1962-1970; Sep. 2013, 10 pages.
The extended European Search Report issued in European Patent Application No. 15811504.8 dated Dec. 19, 2017, 8 pages.
International Preliminary Report on Patentability of International Application No. PCT/JP2015/068198, dated Dec. 27, 2016, total 8 pages.
International Preliminary Report on Patentability of International Application No. PCT/JP2015/068199, dated Dec. 27, 2016, total 12 pages.
Office Action Issued in the corresponding Philippine patent application No. 1/2016/502531, dated Dec. 17, 2018, 5 pages.
Office Action Issued in the corresponding Russian patent application No. 2017101995, with English translation, dated Dec. 11, 2018, 18 pages.
Chinese Office Action issued in Chinese Application No. 201580033814.8, dated Aug. 23, 2019, 12 pages including English translation.
Office Action issued for Indian Patent Application No. 201747002050, dated Apr. 7, 2021, 7 pages.

* cited by examiner

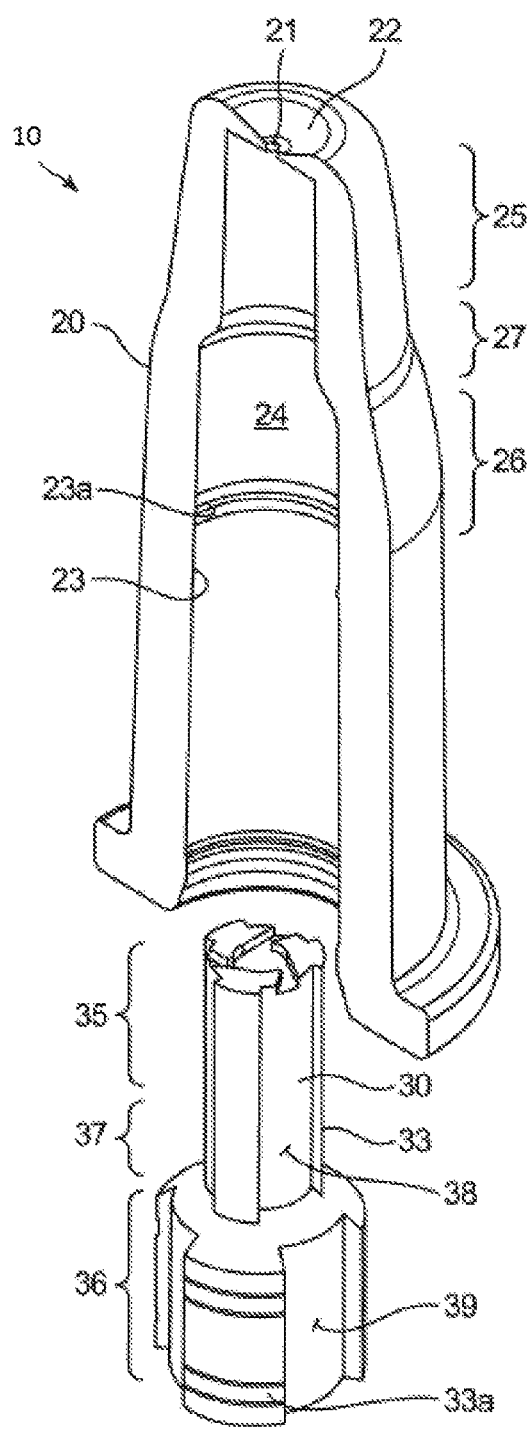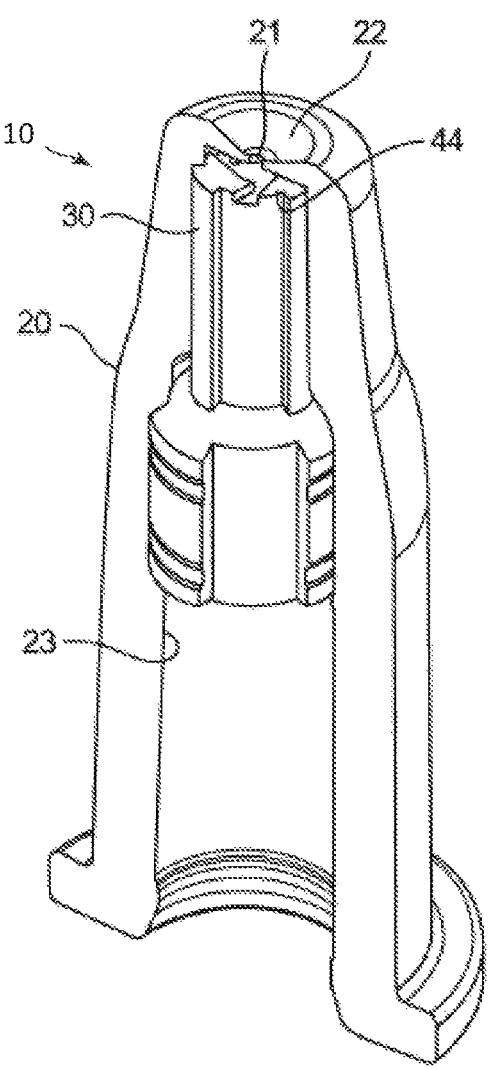

Fig. 8

| Base Material A (PBS) | | | | | |
|---|---|---|---|---|---|
| OK<br>nozzle b<br>diameter φ=0.25 mm<br>thickness d=0.25 mm<br>NO curved portion | OK<br>nozzle b<br>diameter φ=0.25 mm<br>thickness d=0.25 mm<br>NO curved portion | NG<br>nozzle c<br>diameter φ=0.26 mm<br>thickness d=0.23 mm<br>YES curved portion | NG<br>nozzle d<br>diameter φ=0.30 mm<br>thickness d=0.13 mm<br>NO curved portion | OK<br>nozzle e<br>diameter φ=0.30 mm<br>thickness d=0.20 mm<br>NO curved portion | OK<br>nozzle f<br>diameter φ=0.30 mm<br>thickness d=0.30 mm<br>NO curved portion |
| NG<br>nozzle g<br>diameter φ=0.30 mm<br>thickness d=0.25 mm<br>YES curved portion | OK<br>nozzle h<br>diameter φ=0.40 mm<br>thickness d=0.25 mm<br>NO curved portion | NG<br>nozzle i<br>diameter φ=0.40 mm<br>thickness d=0.25 mm<br>YES curved portion | NG<br>nozzle j<br>diameter φ=0.45 mm<br>thickness d=0.25 mm<br>NO curved portion | NG<br>nozzle k<br>diameter φ=0.55 mm<br>thickness d=0.25 mm<br>NO curved portion | |

Fig. 9

Base Material B1

| OK | OK | NG | NG | OK | OK |
|---|---|---|---|---|---|
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.25 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |

| NG | OK | NG | NG | NG | |
|---|---|---|---|---|---|
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |

Fig. 10

Base Material C1

| NG | NG | NG | NG | NG | NG |
|---|---|---|---|---|---|
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.25 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
| NG | NG | NG | NG | NG | |
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |

Fig. 11

Base Material C2

| NG | NG | NG | OK | OK | NG |
|---|---|---|---|---|---|
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.25 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
| ● | ● | ● | ● | ● | ● |
| NG | NG | NG | NG | NG | |
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |
| ⊙ | ● | ⊙ | ● | ⊙ | |

Fig. 12

Base Material D

| | nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.25 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
|---|---|---|---|---|---|---|
| | NG | NG | NG | NG | NG | NG |
| | nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |
| | NG | NG | NG | NG | NG | |

Fig. 13

Base Material E1

| | | | | | |
|---|---|---|---|---|---|
| OK | NG | OK | OK | OK | OK |
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.25 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
| NG | OK | OK | OK | OK | |
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |

Fig. 14

| Base Material E2 | | | | | |
|---|---|---|---|---|---|
| OK | OK | OK | OK | OK | NG |
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.26 mm<br>thickness d=0.35 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
| NG | OK | OK | OK | OK | |
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.23 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |

Fig. 15

| Base Material E4 | | | | | |
|---|---|---|---|---|---|
| OK | OK | NG | OK | OK | OK |
| nozzle a<br>diameter φ=0.25 mm<br>thickness d=0.15 mm<br>NO curved portion | nozzle b<br>diameter φ=0.25 mm<br>thickness d=0.25 mm<br>NO curved portion | nozzle c<br>diameter φ=0.25 mm<br>thickness d=0.35 mm<br>YES curved portion | nozzle d<br>diameter φ=0.30 mm<br>thickness d=0.13 mm<br>NO curved portion | nozzle e<br>diameter φ=0.30 mm<br>thickness d=0.20 mm<br>NO curved portion | nozzle f<br>diameter φ=0.30 mm<br>thickness d=0.30 mm<br>NO curved portion |
| NG | OK | OK | OK | OK | |
| nozzle g<br>diameter φ=0.30 mm<br>thickness d=0.25 mm<br>YES curved portion | nozzle h<br>diameter φ=0.40 mm<br>thickness d=0.25 mm<br>NO curved portion | nozzle i<br>diameter φ=0.40 mm<br>thickness d=0.25 mm<br>YES curved portion | nozzle j<br>diameter φ=0.45 mm<br>thickness d=0.25 mm<br>NO curved portion | nozzle k<br>diameter φ=0.55 mm<br>thickness d=0.25 mm<br>NO curved portion | |

RHINAL SPRAY NOZZLE USED FOR MEDICAL SYRINGE

TECHNICAL FIELD

The present invention relates to a rhinal spray nozzle used for a medical syringe to apply a viscous pharmaceutical formulation to a rhinal mucosal membrane.

BACKGROUND ART

So far a metered-dose syringe-based squirt has been suggested for application as a rhinal spray nozzle. For example, Patent Document 1 (i.e., WO 2013/145789 A1) discloses the metered-dose syringe squirt which comprises a syringe, a plunger being squeezable within the syringe, an elastic-deformation member being elastically deformable by squeezing the plunger within the syringe, and a stopper which is stopped against the syringe and released by restoring force of the elastic-deformation member, whereby the fluid content filled in the single syringe can be delivered at multiple steps by squeezing and releasing the plunger.

Also, although it is not the syringe-based squirt, an airless spray container (e.g., rhinal spray container) has also been proposed to apply a viscous pharmaceutical formulation to a rhinal mucosal membrane. For example, Patent Document 2 (JP 5185109 B) discloses an upside back-pressure airless spray container being operable to control a spray angle and a spray distribution in a desired range thereof when spraying a gel base material comprising carboxy vinyl polymer which was treated by applying an exogenous shear force.

SUMMARY OF INVENTION

Problems to be Solved by Invention

The airless spray container being capable of delivering a multiple metered-dose formulation has an advantage in containing and storing a plurality of formulation doses therein. However in case where the pharmaceutical formulation is used as a prophylaxis or a therapeutic medication for an infectious disease, most of patients or vaccine recipients feel less comfortable and less sanitary to share the airless spray container with the nozzle inserted within their nasal cavities, which may also cause any other infectious diseases (in-hospital infections).

The present inventors have considered to use the metered-dose syringe squirt of the aforementioned Patent Document 1 for spraying the formulation containing the gel base material comprising carboxy vinyl polymer treated by applying an exogenous shear force. However because the metered-dose syringe squirt has a basic structure different from that of the upside back-pressure airless spray container (especially the spray nozzle thereof) disclosed in the aforementioned Patent Document 2, a particular spray characteristics such as a particle size distribution of formulation, an uniform spray geometry, and a spray angle which is required for a targeted pharmaceutical benefits of the formulation has not been achieved so far.

To address the aforementioned drawbacks, the present inventors has finally made the present invention after finding an optimized shape and configuration of the nozzle of the metered-dose syringe-based squirt for spraying the viscous formulation having pre-described features to the rhinal mucosal membrane.

Means to Solve the Problems

One of aspects of the present invention is to provide a rhinal spray nozzle used for a medical syringe having a tip opening in fluid communication with a syringe barrel for storing a formulation, the rhinal spray nozzle comprises a hollow nozzle body having a tip portion defining a nozzle orifice thereon, a solid packing rod arranged within the nozzle body, and a nozzle chamber defined between the packing rod and the nozzle body to allow a fluid communication between the tip opening and the nozzle orifice, wherein the formulation comprises the gel material containing viscosity modification agent and carboxy vinyl polymer of which viscosity is modified by applying an exogenous shear force, and wherein the nozzle orifice has a diameter in a range between 0.25 mm and 0.30 mm.

Preferably, the formulation comprises the gel material containing the viscosity modification agent such as sodium chloride or potassium chloride), a pH buffer solution such as dibasic sodium phosphate hydrate and sodium dihydrogenphosphate, and a neutralizing agent such as L-Arginine and sodium hydroxide, of which viscosity is modified by applying an exogenous shear force.

Also preferably the nozzle orifice includes substantially no curved portion, and the tip portion has thickness along an injection direction of the formulation which is in a range between 0.20 mm and 0.30 mm.

Also preferably the nozzle body includes an inner wall having at least a portion formed in a cylindrical shape and the packing rod includes an outer wall at least a portion formed in a cylindrical shape having a plurality of circumferentially spaced grooves, the nozzle chamber is defined between the at least portion of the inner wall of the nozzle body and the at least portion of the outer wall of the packing rod, and the packing rod includes a vortex-flow generation member opposed to the tip portion of the nozzle body. The vortex-flow generation member formed so that a flow direction of the formulation from the grooves of the packing rod may be offset to a central axis, thereby to generate a vortex flow of the formulation. Also preferably, the at least portion of the inner wall of the nozzle body is formed to have a cross section perpendicular to the injection direction continuously or step-wisely reducing towards the injection direction.

The gel material preferably has a viscosity of 2500 mPas or less, and more preferably 1000 mPas. Preferably a spray angle of the formulation sprayed from the nozzle orifice is in a range 45 degrees and 60 degrees, an average particle size of formulation droplets sprayed from the nozzle orifice is in a range 50 microns and 80 microns. Also preferably, counts of formulation droplets sprayed from the nozzle orifice having the particle size in a range between 10 to 100 microns are 70% or more of the total counts of the particle.

Advantages of Invention

According to the present invention, it is advantageous to achieve the given spray characteristics (a particle size distribution, an uniform spray geometry, and a spray angle) required to obtain a pharmaceutical benefits of the formulation comprising the gel material containing viscosity modification agent and carboxy vinyl polymer of which viscosity is modified by applying an exogenous shear force.

BRIEF DESCRIPTION OF DRAWINGS

FIGS. 2A and 2B are partially-fragmented perspective views of the general structure of the rhinal spray nozzle of one embodiment of the present invention, showing configurations before and after the packing rod are inserted within the nozzle body, respectively.

FIG. 8 shows the spray patterns of the formulation comprising the base materials A in the metered-dose syringe-based squirt provided with various rhinal spray nozzles, and also indicate whether the combination of the base material and the rhinal spray nozzles is acceptable or not.

FIG. 9 shows the spray patterns of the formulation comprising the base materials B1 in the metered-dose syringe-based squirt provided with various rhinal spray nozzles.

FIG. 10 shows the spray patterns of the formulation comprising the base materials C1 in the metered-dose syringe-based squirt provided with various rhinal spray nozzles.

FIG. 11 shows the spray patterns of the formulation comprising the base materials C2 in the metered-dose syringe-based squirt provided with various rhinal spray nozzles.

FIG. 12 shows the spray patterns of the formulation comprising the base materials D in the metered-dose syringe-based squirt provided with various rhinal spray nozzles.

FIG. 13 shows the spray patterns of the formulation comprising the base materials E1 in the metered-dose syringe-based squirt provided with various rhinal spray nozzles.

FIG. 14 shows the spray patterns of the formulation comprising the base materials E2 in the metered-dose syringe-based squirt provided with various rhinal spray nozzles.

FIG. 15 shows the spray patterns of the formulation comprising the base materials E4 in the metered-dose syringe-based squirt provided with various rhinal spray nozzles.

DESCRIPTION OF EMBODIMENTS

With reference to attached drawings, embodiments of a rhinal spray nozzle used for a medical syringe according to the present invention will be described hereinafter. In the following description, directional terms such as "front, "rear", "proximal" and "distal" are conveniently used for better understandings, however those terms are not intended to limit the scope of the present invention. Also, like components are denoted by like reference signs throughout the attached drawings.

[Medical Syringe]

Figure 1:
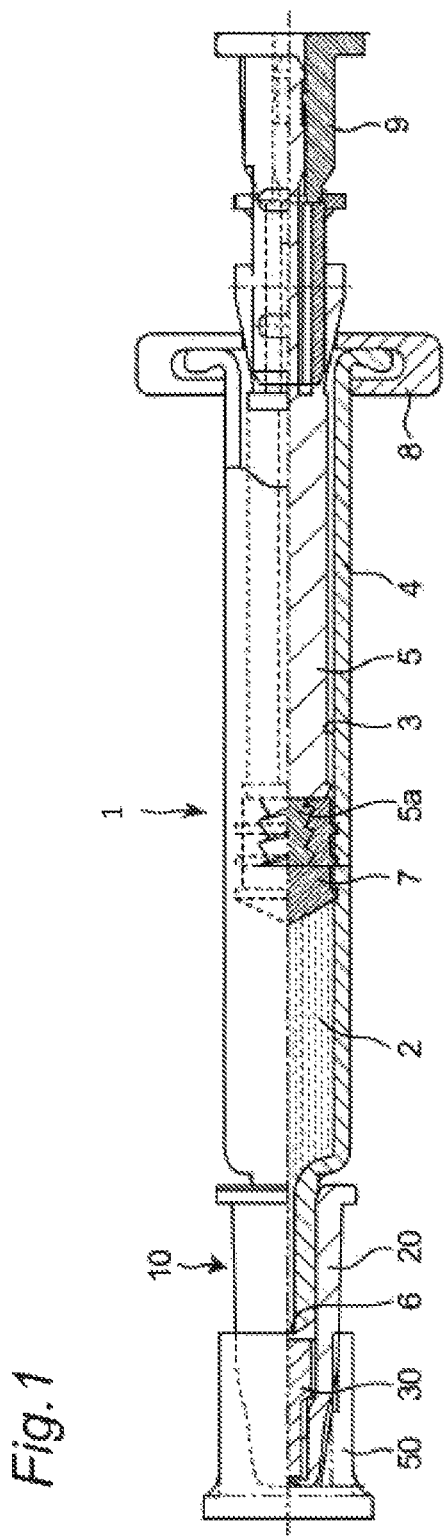
FIG. 1 is a partially-fragmented side view of a general structure of a medical syringe comprising a rhinal spray nozzle of one embodiment according to the present invention.

FIG. 1 is a partially-fragmented side view of a medical syringe 1 comprising a rhinal spray nozzle 10 of an embodiment according to the present invention. As illustrated in FIG. 1, the medical syringe 1 generally comprises a syringe body 4 made of synthetic resin or glass having a syringe barrel 3 capable of storing a pharmaceutical formulation therein, and a plunger rod 5 inserted within the syringe barrel 3 of the syringe body 4. The medical syringe 1 also comprises a piston 7 having a fixing member 5a provided at the distal end of the plunger rod 5 and sliding within the syringe barrel 3 so as to pump the formulation in the syringe barrel 3 out of a distal tip opening 6 of the syringe body 4, a finger flange 8 provided around a proximal end of the syringe body 4, and a plunger end member 9 transmitting the force applied by a practitioner such as a medical doctor to the plunger rod 5. The medical syringe 1 may be similar to the metered-dose syringe-based squirt of the aforementioned Patent Document 1.

It should be noted that the rhinal spray nozzle 10 of the present invention may be applicable to any type of the medical syringes 1 which pump the formulation in the syringe barrel 3 by pushing the plunger rod 5 (and the piston 7), and thus, the present invention will not be limited to the known configurations of the medical syringe. Therefore, the present disclosure will eliminate further description for the detailed structure of the medical syringe (or the metered-dose syringe-based squirt) 1, and discuss in more detail about the structure and the function of the rhinal spray nozzle 10 used for the medical syringe. It should be noted that the disclosure of the aforementioned Patent Document 1 is incorporated herein by reference into the present application.

[Rhinal Spray Nozzle]

As shown in FIG. 1, the medical syringes 1 further comprises the rhinal spray nozzle 10 opposed to the tip opening 6 of the syringe body 4, and a protection cap 50 for protecting a sterilized tip portion 22 of the rhinal spray nozzle 10 from contaminant and mechanical impact. FIGS. 2A and 2B are partially-fragmented perspective views, showing the general structure of the rhinal spray nozzle 10 of an embodiment of the present invention. As shown, the rhinal spray nozzle 10 generally comprises a hollow nozzle body 20 having the tip portion 22 with a nozzle orifice 21 and a solid packing rod (packing bar) 30 provided within the nozzle body 20. FIGS. 2A and 2B show the rhinal spray nozzle 10 before and after the packing rod 30 is arranged or inserted within the nozzle body 20, respectively. The tip portion 22 of the nozzle body 20 has a circular shape and is provided with the nozzle orifice 21 at the center thereof.

Figure 3A:
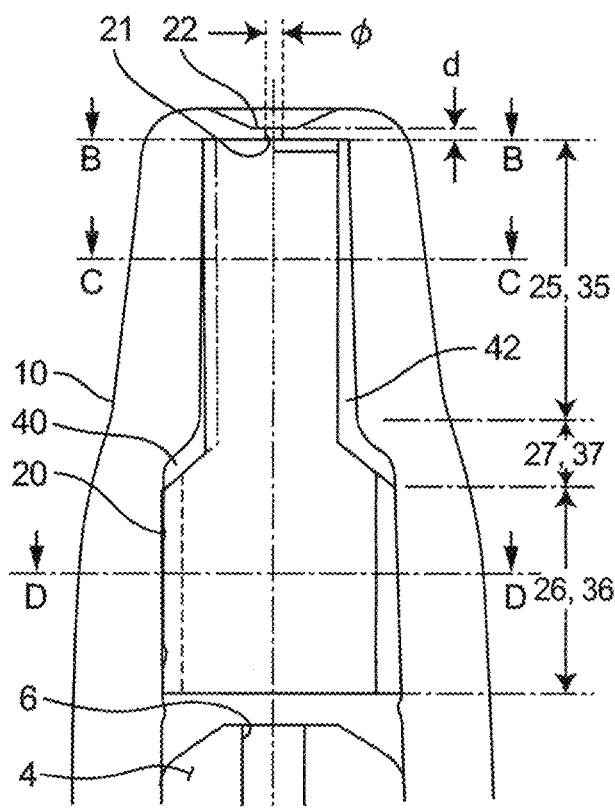
FIG. 3A is a vertical cross-sectional view of the rhinal spray nozzle of FIG. 2B, and FIGS. 3B, 3C and 3D are horizontal cross-sectional views of the rhinal spray nozzle taken along B-B line, C-C line and D-D line of FIG. 3A, respectively.
Figure 3B:
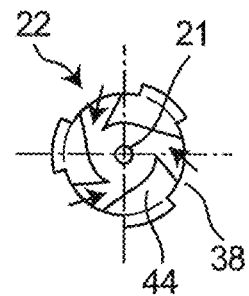
Figure 3C:
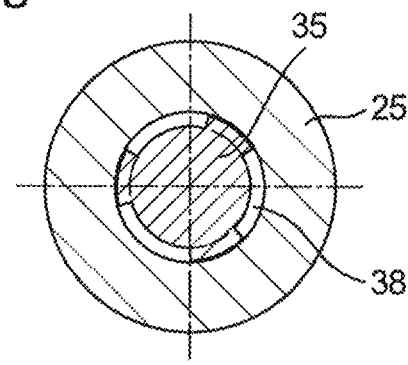
Figure 3D:
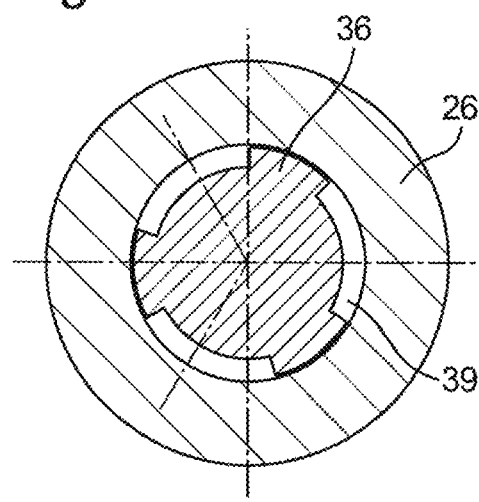

FIG. 3A is a vertical cross-sectional view of the rhinal spray nozzle 10 of FIG. 2B. FIGS. 3B, 3C and 3D are horizontal cross-sectional views of the rhinal spray nozzle 10 taken along B-B line, C-C line and D-D line of FIG. 3A, respectively. The hollow nozzle body 20 defines an internal space 24 of a substantially cylindrical shape. As shown in FIGS. 3C and 3D, the internal space 24 includes a nozzle small-diameter portion 25 closer to the nozzle orifice 21 of the hollow nozzle body 20, a nozzle large-diameter portion 26 opposing to the tip opening 6 of the syringe body 4, and a nozzle shoulder 27 which is designed to have a diameter continuously or step-wisely reducing from the nozzle large-diameter portion 26 towards the nozzle small-diameter portion 25.

On the other hand, the solid packing rod 30 to be inserted within the nozzle body 20 has an outer wall 33 having a configuration substantially complementary with an inner wall 23 of the nozzle body 20 (internal space 24). As shown in FIGS. 2A, 3C and 3D, a rod small-diameter portion 35 and a rod large-diameter portion 36 include shoulder 37 which is designed to have a diameter continuously or step-wisely reducing from a rod large-diameter portion 36 towards a rod small-diameter portion 35.

Preferably, as illustrated in FIG. 3A, the inner wall 23 of the nozzle body 20 is provided with a protrusion 23a, while the outer wall 33 of the packing rod 30 is provided with a recess 33a for receiving the protrusion 23a. When the packing rod 30 is fully inserted within the internal space 24 of the nozzle body 20, the protrusion 23a may be closely fit in the recess 33a to ensure connection between the packing rod 30 and the nozzle body 20.

Also as illustrated in FIGS. 2A-2B and 3A-3D, the packing rod 30 includes a plurality of grooves 38, 39 circumferentially spaced from one another both on the rod small-diameter portion 35 and the rod large-diameter portion 36. Also, the packing rod 30 is inserted within the nozzle body 20 so as to define a gap 40 between the nozzle shoulder 27 and the rod shoulder 37 (FIG. 3A). Thus, the rhinal spray nozzle 10 assembled as illustrated in FIG. 2B has a nozzle chamber 42 defined by the grooves 38, 39 and the gap 40 which allows fluid communication of the formulation 2 delivered from the tip opening 6 of the syringe body 4 through the nozzle chamber 42 to the tip portion 22 of the rhinal spray nozzle 10.

Furthermore, as shown in FIG. 3B, the packing rod 30 includes a vortex-flow generation member 44 opposed to the tip portion 22 of the rhinal spray nozzle 10. The vortex-flow generation member 44 is configured to generate a vortex flow of the formulation 2 that is delivered from each of the grooves 38 of the rod small-diameter portion 35 before being injected from the nozzle orifice 21 of the nozzle body 20. More particularly, the end portions of the rod small-diameter portion 35 which define the vortex-flow generation member 44 are formed so as to extend offset the vertical central axis of the nozzle orifice 21. Thanks to generation of the vortex flow of the formulation 2 before being injected from the nozzle orifice 21, the spray angle of the formulation 2 can be expanded to spray it in a more uniform manner.

As illustrated in FIGS. 3C-3D, it is preferable to design the grooves 38 of the rod small-diameter portion 35 to be less than the grooves 39 of the rod large-diameter portion 36 so as to increase the pressure of the formulation 2 in the vortex-flow generation member 44 before being injected from the nozzle orifice 21. Also, thanks to the diameters of the rod large-diameter portion 36 and the rod small-diameter portion 35 which are designed to continuously or step-wisely be reduced from the former to the latter, it is easier to insert the rhinal spray nozzle 10 deeply into the nasal cavity and to spray the formulation towards the inferior nasal concha and even deeper portions of the patient. Thus preferably, the diameter of the rod small-diameter portion 35 is smaller enough than the nasal cavity opening of the patient without minimizing fear of the patient.

[Optimal Spray of Formulation into Nasal Cavity]

In general, when a fluid such as a phosphate buffered saline (PBS) having substantially no viscosity is sprayed towards the inferior nasal concha by means of the medical syringe 1 through the rhinal spray nozzle 10 of the above embodiment, the fluid immediately comes out from the nasal cavity or runs out from the uvula pharyngeal portion through the inferior nasal meatus of the patient, because of lack of retention characteristic of the fluid. Thus, in order to keep the sprayed formulation retained on the inferior nasal concha of the patient, the formulation is required to have a predetermined viscosity. Also in general, the viscosity of the formulation is likely reduced during passing through the spray nozzle, and therefore, in order to maintain the desired spray retention characteristic of the formulation, it is necessary to maintain the viscosity thereof not only before being sprayed but also immediately after being sprayed.

Figure 5:
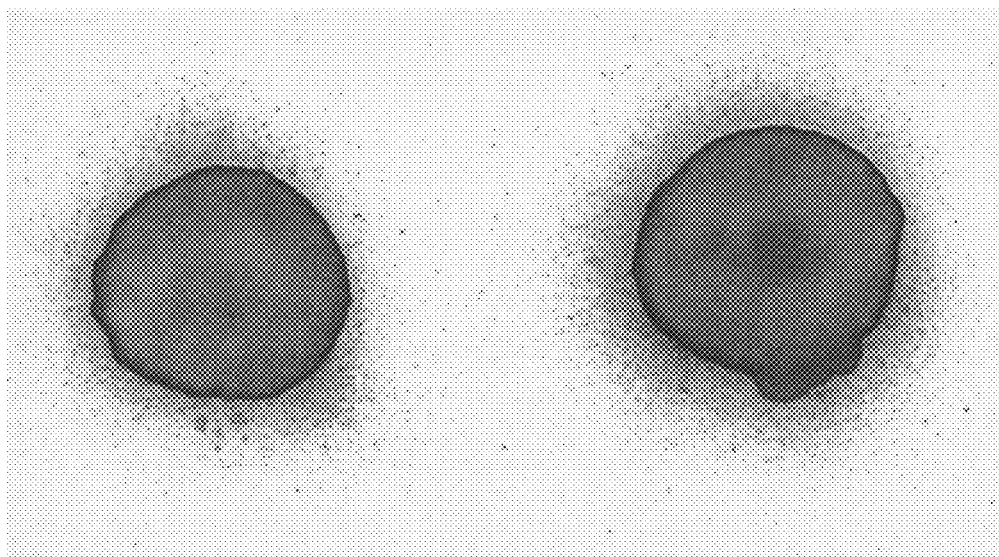
FIG. 5 shows spray patterns of the formulation sprayed from the nozzle orifice of Example 1.

Also, besides the spray retention characteristic, appropriate characteristics for an uniform spray geometry, a spray angle, and a particle size distribution (i.e., an average particle size) of the formulation are required when it is applied by the medical syringe 1 using the rhinal spray nozzle 10. In particular, the uniform spray geometry of the formulation is referred to as a characteristic where the sprayed formulation is distributed in a substantially uniform concentration, and is evaluated with a sprayed pattern on a plane arranged perpendicularly to the spraying direction of the formulation injected from the nozzle orifice 21. Thus, the present disclosure evaluates the sprayed pattern as being acceptable (abbreviated as "OK") with the formulation for the rhinal spray nozzle 10 of the present invention when having substantially a circular or full-cone shape as illustrated in FIG. 5, and as being unacceptable (abbreviated as "NG") when having an oblong or hollow-cone shape.

The spray angle is referred to as the maximum dispersing angle of the sprayed formulation droplet (which may be referred to as a "formulation particle"), and the present disclosure evaluates the spray angle as being acceptable (abbreviated as "OK") with the formulation for the rhinal spray nozzle 10 of the present invention when the formulation falls within a range between 40 to 60 degrees.

Furthermore in general, the formulation particles cannot be delivered to the inferior nasal concha of the patient when being too big, meanwhile they are likely inhaled to the bronchi and/or the lung of the patient upon breathing when being too fine. In either case, the expected therapeutic benefits of the formulation cannot be achieved. Therefore, the present disclosure evaluates the average particle size as being acceptable (abbreviated as "OK") with the formulation for the rhinal spray nozzle 10 of the present invention when the average particle size falls within a range between 50 to 80 microns and the counts of the particles having the particle size in a range between 10 to 100 microns are 70% or more of the total counts of the particles.

EXAMPLES

As will be described in detail, several rhinal spray nozzles 10 having different sizes and/or shapes which is used for the medical syringe 1 were prepared to evaluate whether the rhinal spray nozzles 10 are acceptable or not (OK or NG) when spraying various formulations containing the gel base materials, by checking the viscosity and/or viscosity retention rate (or the spray retention characteristic), the spray uniformity (or the spray pattern), the spray angle, and the average particle size of the formulations.

[Preparation of Rhinal Spray Nozzles]

Several rhinal spray nozzles 10a-10k capable of being connected to the medical syringe 1 of the aforementioned embodiment were produced, by modifying the diameter (φ) of the nozzle orifice 21 and the thickness (d) of the tip portion 22 along the injection direction of the formulation, and by providing a curved portion or not on the tip portion 22 (yes or no).

TABLE 1

| | Nozzle a | Nozzle b | Nozzle c | Nozzle d | Nozzle e | Nozzle f | Nozzle g | Nozzle h | Nozzle i | Nozzle j | Nozzle k |
|---|---|---|---|---|---|---|---|---|---|---|---|
| orifice diameter φ | 0.25 | 0.25 | 0.26 | 0.3 | 0.3 | 0.3 | 0.3 | 0.4 | 0.4 | 0.45 | 0.55 |
| thickness d | 0.15 | 0.25 | 0.25 | 0.13 | 0.2 | 0.3 | 0.25 | 0.25 | 0.25 | 0.25 | 0.25 |
| curved portion | no | no | yes | no | no | no | yes | no | yes | no | no |

(unit: mm)

Figure 4A:
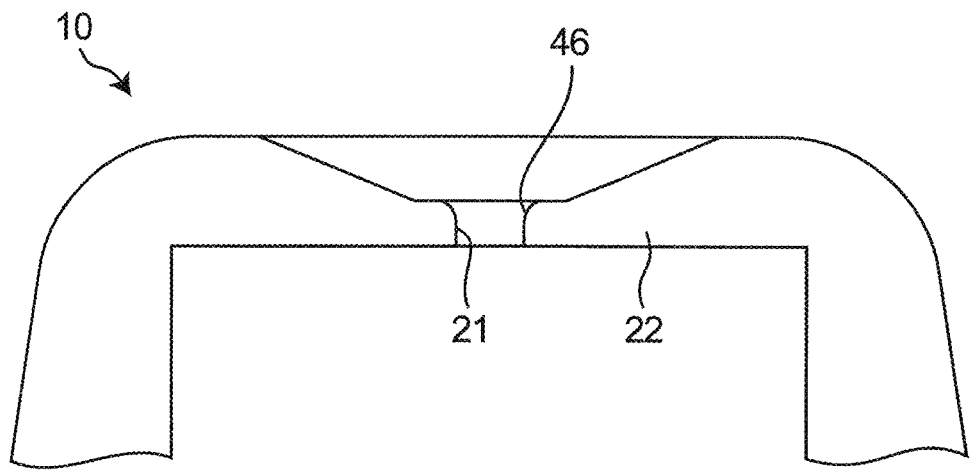
FIGS. 4A and 4B are enlarged cross-sectional views of the tip portion of the nozzle body, in which the tip portion is provided with the curved portion in FIG. 4A but not in FIG. 4B.
Figure 4B:
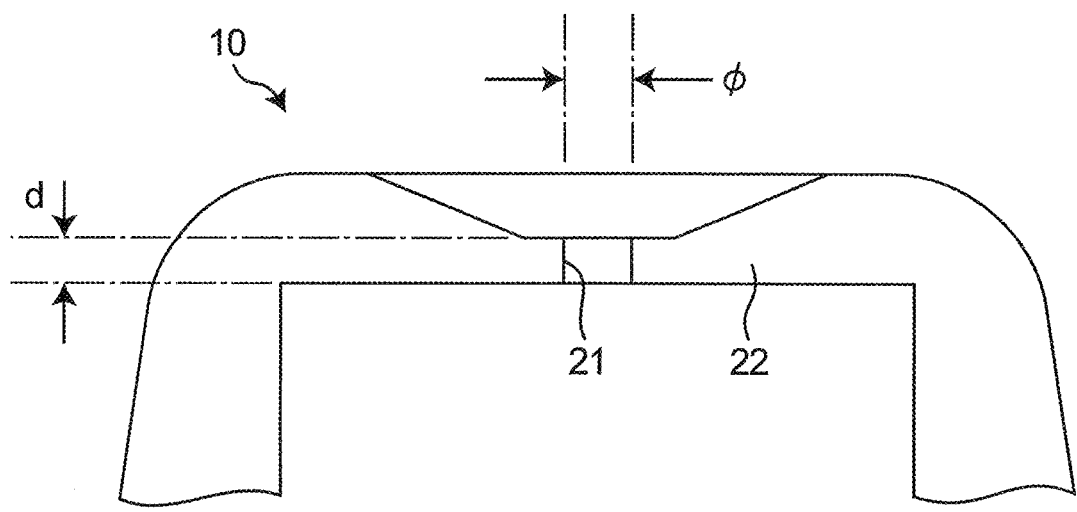

FIGS. 4A and 4B are enlarged cross-sectional views of the tip portion 22 of the nozzle body 20, in which the tip portion 22 is provided with the curved portion 46 in FIG. 4A (yes) but not in FIG. 4B (no). Each of the rhinal spray nozzles 10a-10k includes the nozzle orifices 21 having the diameters (φ) in the range between 0.25 mm to 0.55 mm, and the tip portion 22 having the thickness (d) in the range between 0.13 mm to 0.30 mm along the injection direction of the formulation. The rhinal spray nozzles 10c, 10g, 10i each have the curved portion 46 with the tip portion 22 as illustrated in FIG. 4A.

[Preparation of Various Formulations Containing Base Material]

Next, various formulations to be sprayed by means of the medical syringe 1 with the aforementioned rhinal spray nozzles 10 were prepared in following prescriptions.

[Base Material A]:
a phosphate buffered saline (Reference example),

[Base Material B]:
a base material obtained by modifying an amount of carboxy vinyl polymer to have a given viscosity,

[Base Material C]:
a base material obtained by adding a viscosity modification agent (sodium chloride) to have a given viscosity,

[Base Material D]:
a base material obtained by applying an exogenous shear force to have a given viscosity, and

[Base Material E]:
a base material obtained adding a viscosity modification agent (sodium chloride) and by applying an exogenous shear force to have a given viscosity.

With respect to the base materials D and E, the exogenous shear force may be applied in any process, and although not limited thereto, it may be applied by preparing, mixing components of the base material, blending them to be homogeneous, and rotating it at a relatively high speed by means of an intermittent jet stream generation type high-speed emulsification device. Also the base materials so processed may further be heat-treated and sterilized in an atmosphere of high-pressure steam.

TABLE 2

| Base Material A (Reference Example) | |
|---|---|
| Phosphate Buffered Saline | |
| Viscosity | 1 mPas |
| Viscosity Retention Rate | (N/A) |

TABLE 3

| Base Material B1 | |
|---|---|
| Carboxy Vinyl Polymer | 0.07425 wt % |
| L-Arginine | 0.08505 wt % |
| Purified Water | 99.8407 wt % |
| Viscosity | 2500 mPas |

TABLE 3-continued

| | |
|---|---|
| Viscosity Retention Rate | 28.4% |
| prepared by modifying an amount of carboxy vinyl polymer to have viscosity of 2500 mPs | |
| Base Material B2 | |
| Carboxy Vinyl Polymer | 0.0557 wt % |
| L-Arginine | 0.0942 wt % |
| Purified Water | 99.8501 wt % |
| Viscosity | 1000 mPas |
| Viscosity Retention Rate | 17.5% |
| prepared by modifying an amount of carboxy vinyl polymer to have viscosity of 1000 mPs | |

TABLE 4

| Base Material C1 | |
|---|---|
| Carboxy Vinyl Polymer | 0.5 wt % |
| L-Arginine | 1.0 wt % |
| Sodium Chloride | 0.5 wt % |
| Purified Water | 98.0 wt % |
| Viscosity | 2400 mPas |
| Viscosity Retention Rate | 82.6% |
| prepared by adding a viscosity modification agent (Sodium Chloride) to have viscosity of 2400 mPa | |
| Base Material C2 | |
| Carboxy Vinyl Polymer | 0.5 wt % |
| L-Arginine | 1.0 wt % |
| Sodium Chloride | 0.5 wt % |
| Ethanol | 0.5 wt % |
| Purified Water | 97.5 wt % |
| Viscosity | 2400 mPas |
| Viscosity Retention Rate | 81.6% |
| prepared by adding a viscosity modification agent (Sodium Chloride) to have viscosity of 2400 mPa and by adding an ethanol for improving spray pattern | |
| Base Material C3 | |
| Carboxy Vinyl Polymer | 0.375 wt % |
| L-Arginine | 0.7 wt % |
| Sodium Chloride | 0.25 wt % |
| Purified Water | 98.675 wt % |
| Viscosity | 1000 mPas |
| Viscosity Retention Rate | 76.5% |
| prepared by adding a viscosity modification agent (Sodium Chloride) to have viscosity of 1000 mPa | |

TABLE 5

| Base Material D | |
|---|---|
| Carboxy Vinyl Polymer | 0.5 wt % |
| L-Arginine | 1.0 wt % |
| Purified Water | 98.5 wt % |
| Viscosity | 2500 mPas |
| Viscosity Retention Rate | 99.5% |
| prepared by applying an exogenous shear force to have a viscosity of 2500 mPa | |

TABLE 6

Base Material E1

| | |
|---|---|
| Carboxy Vinyl Polymer | 0.5 wt % |
| L-Arginine | 1.0 wt % |
| Sodium Chloride | 0.25 wt % |
| Purified Water | 98.25 wt % |
| Viscosity | 2500 mPas |
| Viscosity Retention Rate | 99.8% | prepared by adding a viscosity modification agent (Sodium Chloride) and by applying an exogenous shear force to have viscosity of 2500 mPa

Base Material E2

| | |
|---|---|
| Carboxy Vinyl Polymer | 0.5 wt % |
| L-Arginine | 1.0 wt % |
| Sodium Chloride | 0.25 wt % |
| Ethanol | 0.5 wt % |
| Purified Water | 97.75 wt % |
| Viscosity | 2400 mPas |
| Viscosity Retention Rate | 98.6% | prepared by adding a viscosity modification agent (Sodium Chloride) and by applying an exogenous shear force to have viscosity of 2500 mPa and by adding an ethanol for improving spray pattern

Base Material E3

| | |
|---|---|
| Carboxy Vinyl Polymer | 0.375 wt % |
| L-Arginine | 0.7 wt % |
| Sodium Chloride | 0.125 wt % |
| Purified Water | 98.8 wt % |
| Viscosity | 1000 mPas |
| Viscosity Retention Rate | 100% | prepared by adding a viscosity modification agent (Sodium Chloride) and by applying an exogenous shear force to have viscosity of 1000 mPa

Base Material E4

| | |
|---|---|
| Carboxy Vinyl Polymer | 0.55 wt % |
| L-Arginine | 1.20 wt % |
| Concentrated Glycerin | 1.00 wt % |
| Dibasic Sodium Phosphate Hydrate | 0.1765 wt % |
| Sodium Dihydrogenphosphate | 0.0270 wt % |
| Sodium Chloride | 0.4250 wt % |
| Purified Water | 69.6215 wt % |
| Viscosity | 1000 mPas |
| Viscosity Retention Rate | 100% | prepared by adding a viscosity modification agent (Sodium Chloride) and by applying an exogenous shear force to have viscosity of 1000 mPa

Example 1

An influenza vaccine composition (the formulation comprising the gel base material E4 containing an inactivated whole-virus antigen influenza vaccine) was prepared by mixing a gel base material and a stock solution of an influenza vaccine as follows.

TABLE 7

Influenza Vaccine Composition
Inactivated Whole-Virus Antigen Influenza Vaccines

| | |
|---|---|
| A/California/7/2009 (H1N1) | 30 µgHA |
| A/Victoria/210/2009 (H3N2) | 30 µgHA |
| B/Brisbane/60/2008 | 60 µgHA |
| Carboxy Vinyl Polymer | 5.50 mg |
| L-Arginine | 12.00 mg |
| oncentrated Glycerin | 10.00 mg |
| Dibasic Sodium Phosphate Hydrate | 1.765 mg |
| Sodium Dihydrogenphosphate | 0.270 mg |
| Sodium Chloride | 4.25 mg |
| Purified Water | proper quantity |
| Total | 1.0 mL |

[Evaluation Process]
a) Viscosity/Viscosity Retention Rate

The viscosity of the base material A-E according to the present embodiment is measured by a C-type viscosimeter at 20 degrees C. The viscosity retention rate is referred to the remaining rate of the viscosity of the base material A-E immediately after being sprayed.

b) Spray Uniformity (Spray Pattern)

After filling each of the base materials A-E in the medical syringe 1 (metered-dose syringe-based squirt) provided with various rhinal spray nozzles 10a-10k, each of the base materials A-E was sprayed from the respective rhinal spray nozzles 10a-10k towards a paper arranged vertically and spaced away from the nozzle orifice 21 by a predetermined distance. For example, FIG. 5 shows the spray patterns being acceptable in a particular combination of the base material and the rhinal spray nozzle 10, both of which have circular shapes (rather than oval shapes) and show uniform full-cone spraying (rather than hollow-cone spraying).

c) Spray Angle

Figure 6:
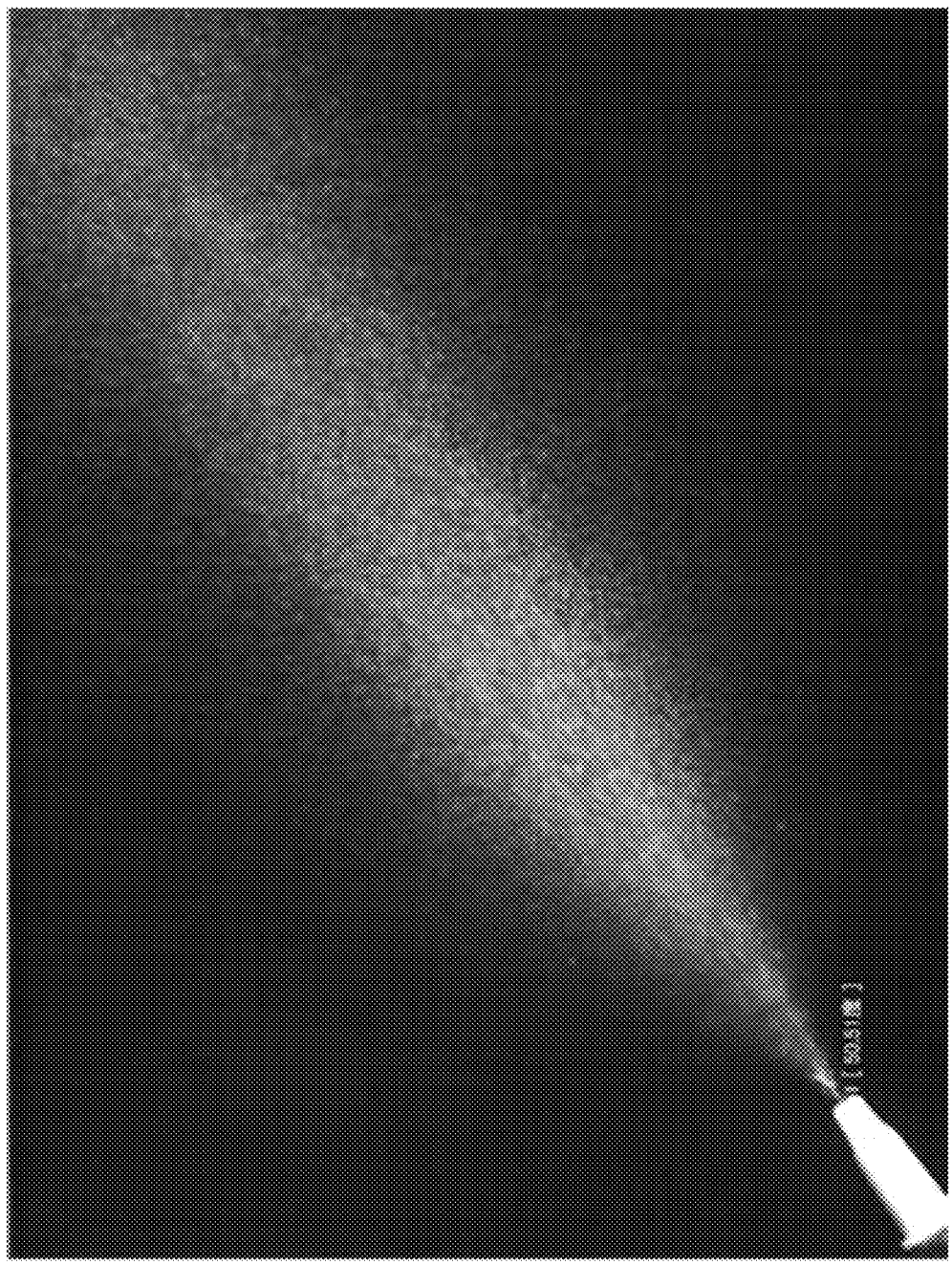
FIG. 6 shows a spray angle of the formulation sprayed from the nozzle orifice of Example 1.

After filling each of the base materials A-E in the medical syringe 1 provided with various rhinal spray nozzles 10a-10k, each of the base materials A-E was sprayed. A high-speed microscope commercially available from Keyence Corporation® (model No. VW-9000) was used to measure the spray angle of the formulation sprayed from the nozzle orifice 21 of each of the rhinal spray nozzles 10a-10k. For example, FIG. 6 shows the spray angle being acceptable in a particular combination of the base material and the rhinal spray nozzle 10, since the spray angle was 50.51 degrees while the desired or acceptable range according to the present disclosure is set between 40-60 degrees.

d) Average Particle Size and Particle Size Distribution

Figure 7:
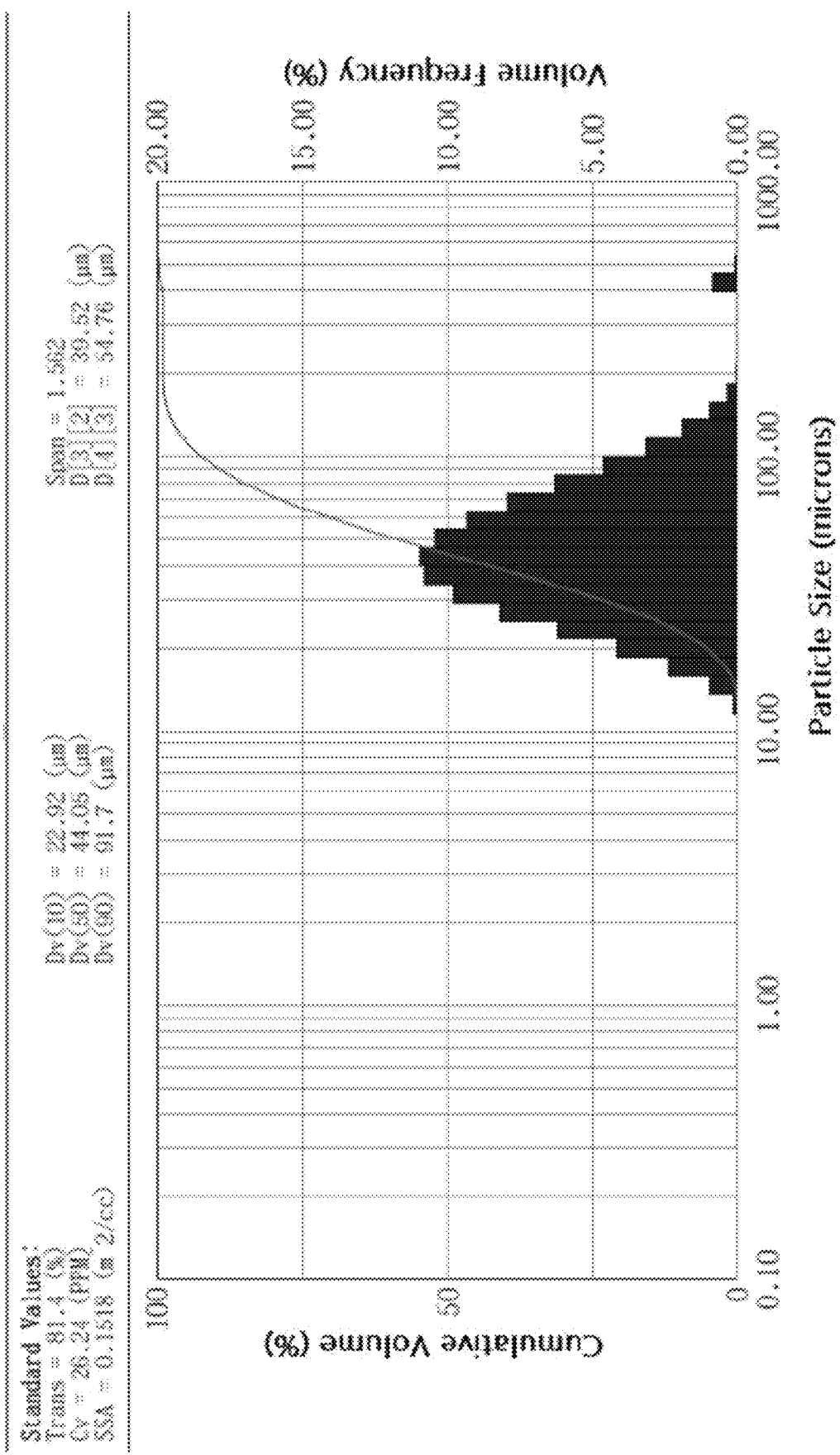
FIG. 7 shows a particle size distribution of the formulation sprayed from the nozzle orifice of Example 1.

Also after filling each of the base materials A-E in the medical syringe 1 (metered-dose syringe-based squirt) provided with various rhinal spray nozzles 10a-10k, each of the base materials A-E was sprayed by pushing the plunger rod 5 at a predetermined speed (e.g., 80 mm/s). A laser-diffraction particle size distribution measuring apparatus was used for measuring the particle size of the formulation sprayed from the nozzle orifice 21 of the rhinal spray nozzles 10a-10k so as to determine the average particle size and the rate or percentage of counts of the particles having the particle size in a range between 10 to 100 microns over the total counts thereof. For example, FIG. 7 shows the average particle size of the sprayed formulation is 56.60 microns and the percentage of counts of the particles having the particle size in a range between 10 to 100 microns over the total counts thereof is 86.90%, which is acceptable in a particular combination of the base material and the rhinal spray nozzle 10.

After filling the base materials A, B1-B2, C1-C3, D, E1-E4 in the medical syringe 1 (metered-dose syringe-based squirt) provided with various rhinal spray nozzles 10a-10k, the test results were obtained as illustrated in Tables 8-10 for:

a) Viscosity (V) and Viscosity Retention Rate (VRR),
b) Spray Pattern (SP),
c) Spray Angle (SA), and
d) Average Particle Size (APS), Particle Size Distribution (PSD), and Percentage of Counts of the particles between 10 to 100 microns (PC).

Similarly, FIGS. 8-15 show the spray patterns of the formulation comprising the base materials A, B1, C1-C2, D, E4 (eight types) in the medical syringe 1 (metered-dose syringe-based squirt) provided with various rhinal spray nozzles 10a-10k, and also indicate whether the combination of each of the base materials and the rhinal spray nozzles is acceptable or not (abbreviated herein as "OK" and "NG").

TABLE 8

|  |  | Nozzle a | Nozzle b | Nozzle c | Nozzle d | Nozzle e | Nozzle f |
|---|---|---|---|---|---|---|---|
|  | orifice diameter | 0.25 | 0.25 | 0.26 | 0.3 | 0.3 | 0.3 |
|  | thickness d | 0.15 | 0.25 | 0.25 | 0.13 | 0.2 | 0.3 |
|  | curved portion | no | no | yes | no | no | no |
| Base Material A (PBS) | V = 1 mPs VRR (N/A) | OK | OK | NG | NG | OK | OK |
|  | SP | circular full cone | circular full cone | circular semi-hollow cone | circular full cone | circular full cone | circular full cone |
|  | SA | 60 degrees | 55 degrees | 75 degrees | 73 degrees | 58 degrees | 55 degrees |
|  | APS | 57 μm | 64 μm | 71 μm | 55 μm | 59 μm | 66 μm |
|  | PSD | 90% or more | 90% or more | 80% or more | 90% or more | 90% or more | 90% or more |
|  | PC | −94.20% | −92.00% | −88.60% | −96.30% | −92.40% | −90.20% |
| Base Material B1 | V = 2500 mPs VRR = 28.4% | OK | OK | NG | NG | OK | OK |
|  | SP | circular full cone | circular full cone | circular hollow cone | circular fall cone | circular full cone | circular full cone |
|  | SA | 50 degrees | 45 degrees | 75 degrees | 62 degrees | 58 degrees | 55 degrees |
|  | APS | 69 μm | 77 μm | 79 μm | 68 μm | 58 μm | 56 μm |
|  | PSD | 90% or more | 80% or more | 80% or more | 90% or more | 90% or more | 90% or more |
|  | PC | −92.10% | −88.40% | −83.90% | −91.10% | −96.20% | −94.90% |
| Base Material B2 | V = 1000 mPS VRR = 17.5% | OK | OK | NG | NG | OK | OK |
|  | SP | circular full cone | circular full cone | circular hollow cone | circular full cone | circular full cone | circular full cone |
|  | SA | 56 degrees | 53 degrees | 78 degrees | 71 degrees | 60 degrees | 63 degrees |
|  | APS | 63 μm | 70 μm | 76 μm | 55 μm | 61 μm | 59 μm |
|  | PSD | 90% or more | 80% or more | 80% or more | 90% or more | 90% or more | 90% or more |
|  | PC | −94.00% | −88.90% | −88.40% | −93.30% | −93.80% | −95.50% |
| Base Material C1 | V = 2400 mPs VRR = 82.6% | NG | NG | NG | NG | NG | NG |
|  | SP | circular semi-hollow cone | circular semi-hollow cone | circular semi-hollow cone | circular hollow cone | circular semi-hollow cone | circular semi-hollow cone |
|  | SA | 76 degrees | 72 degrees | 62 degrees | 79 degrees | 61 degrees | 50 degrees |
|  | APS | 66 μm | 68 μm | 72 μm | 64 μm | 69 μm | 63 μm |
|  | PSD | 80% or more | 80% or more | 80% or more | 80% or more | 80% or more | 80% or more |
|  | PC | −84.10% | −82.70% | −83.50% | −81.60% | −82.80% | −83.30% |

|  |  | Nozzle g | Nozzle h | Nozzle i | Nozzle j | Nozzle k |
|---|---|---|---|---|---|---|
|  | orifice diameter | 0.3 | 0.4 | 0.4 | 0.45 | 0.55 |
|  | thickness d | 0.25 | 0.25 | 0.25 | 0.25 | 0.25 |
|  | curved portion | yes | no | yes | no | no |
| Base Material A (PBS) | V = 1 mPs VRR (N/A) | NG | OK | NG | NG | NG |
|  | SP | circular hollow cone | circular full cone | circular hollow cone | circular hollow cone | circular hollow cone |
|  | SA | 75 degrees | 58 degrees | 76 degrees | 76 degrees | 80 degrees |
|  | APS | 72 μm | 69 μm | 77 μm | 74 μm | 73 μm |
|  | PSD | 80% or more | 90% or more | 80% or more | 80% or more | 80% or more |
|  | PC | −86.70% | −91.40% | −83.30% | −81.60% | −80.60% |
| Base Material B1 | V = 2500 mPs VRR = 28.4% | NG | OK | NG | NG | NG |
|  | SP | circular hollow cone | circular full cone | circular hollow cone | circular semi-hollow cone | circular semi-hollow cone |
|  | SA | 82 degrees | 58 degrees | 77 degrees | 72 degrees | 72 degrees |
|  | APS | 76 μm | 70 μm | 76 μm | 80 μm | 84 μm |
|  | PSD | 80% or more | 90% or more | 80% or more | 70% or more | 70% or more |
|  | PC | −83.80% | −92.80% | −84.40% | −78.90% | −76.80% |
| Base Material B2 | V = 1000 mPS VRR = 17.5% | NG | OK | NG | NG | NG |
|  | SP | circular hollow cone | circular full cone | circular hollow cone | circular semi-hollow cone | circular semi-hollow cone |
|  | SA | 85 degrees | 65 degrees | 80 degrees | 74 degrees | 75 degrees |
|  | APS | 67 μm | 66 μm | 72 μm | 77 μm | 84 μm |
|  | PSD | 80% or more | 90% or more | 80% or more | 80% or more | 80% or more |
|  | PC | −86.80% | −94.80% | −85.90% | −82.80% | −80.20% |
| Base Material C1 | V = 2400 mPs VRR = 82.6% | NG | NG | NG | NG | NG |
|  | SP | circular hollow cone | circular semi-hollow cone | circular hollow cone | circular hollow cone | circular hollow cone |
|  | SA | 84 degrees | 60 degrees | 70 degrees | 70 degrees | 72 degrees |
|  | APS | 64 μm | 63 μm | 67 μm | 70 μm | 65 μm |

TABLE 8-continued

|  |  |  |  |  |  |  |
|---|---|---|---|---|---|---|
|  | PSD | 80% or more | 80% or more | 80% or more | 70% or more | 70% or more |
|  | PC | −82.80% | −83.70% | −80.60% | −78.80% | −79.40% |

TABLE 9

|  |  | Nozzle a | Nozzle b | Nozzle c | Nozzle d | Nozzle e | Nozzle f |
|---|---|---|---|---|---|---|---|
|  | orifice diameter | 0.25 | 0.25 | 0.26 | 0.3 | 0.3 | 0.3 |
|  | thickness d | 0.15 | 0.25 | 0.25 | 0.13 | 0.2 | 0.3 |
|  | curved portion | no | no | yes | no | no | no |
| Base Material C2 | V = 2400 mPs VRR = 81.6% | NG | NG | NG | OK | OK | NG |
|  | SP | circular semi-hollow cone | oval semi-hollow cone | circular semi-hollow cone | circular full cone | circular full cone | circular full cone |
|  | SA | 65 degrees | 58 degrees | 70 degrees | 53 degrees | 43 degrees | 36 degrees |
|  | APS | 64 μm | 65 μm | 68 μm | 62 μm | 66 μm | 65 μm |
|  | PSD | 80% or more | 80% or more | 80% or more | 80% or more | 80% or more | 80% or more |
|  | PC | −88.80% | −87.90% | −86.80% | −87.40% | −88.3 | −83.00% |
| Base Material C3 | V = 1000 mPs VRR = 76.5% | NG | NG | NG | NG | NG | NG |
|  | SP | circular semi-hollow cone | circular semi-hollow cone | circular semi-hollow cone | circular hollow cone | circular semi-hollow cone | circular semi-hollow cone |
|  | SA | 81 degrees | 78 degrees | 74 degrees | 83 | 68 degrees | 66 degrees |
|  | APS | 65 μm | 66 μm | 69 μm | 67 μm | 64 μm | 64 μm |
|  | PSD | 80% or more | 80% or more | 80% or more | 80% or more | 80% or more | 80% or more |
|  | PC | −86.80% | −88.60% | −84.60% | −87.20% | −86.00% | −87.30% |
| Base Material D | V = 2500 mPs VRR = 99.5% | NG | NG | NG | NG | NG | NG |
|  | SP | oval full cone | oval full cone | oval semi-hollow cone | circular full cone | circular full cone | circular full cone |
|  | SA | 58 degrees | 58 degrees | 58 degrees | 47 degrees | 33 degrees | 39 degrees |
|  | APS | 70 μm | 72 μm | 76 μm | 86 μm | 89 μm | 91 μm |
|  | PSD | 80% or more | 80% or more | 80% or more | 80% or more | 70% or more | 70% or more |
|  | PC | −84.40% | −82.80% | −83.50% | −80.70% | −77.80% | −73.30% |

|  |  | Nozzle g | Nozzle h | Nozzle i | Nozzle j | Nozzle k |
|---|---|---|---|---|---|---|
|  | orifice diameter | 0.3 | 0.4 | 0.4 | 0.45 | 0.55 |
|  | thickness d | 0.25 | 0.25 | 0.25 | 0.25 | 0.25 |
|  | curved portion | yes | no | yes | no | no |
| Base Material C2 | V = 2400 mPs VRR = 81.6% | NG | NG | NG | NG | NG |
|  | SP | circular hollow cone | oval full cone | circular hollow cone | circular semi-hollow cone | circular hollow cone |
|  | SA | 84 degrees | 59 degrees | 68 degrees | 70 degrees | 70 degrees |
|  | APS | 62 μm | 60 μm | 61 μm | 67 μm | 61 μm |
|  | PSD | 80% or more | 80% or more | 80% or more | 80% or more | 80% or more |
|  | PC | −85.80% | −88.70% | −87.20% | −82.20% | −83.70% |
| Base Material C3 | V = 1000 mPs VRR = 76.5% | NG | NG | NG | NG | NG |
|  | SP | circular hollow cone | circular semi-hollow cone | circular hollow cone | circular hollow cone | circular hollow cone |
|  | SA | 82 degrees | 70 degrees | 77 degrees | 76 degrees | 77 degrees |
|  | APS | 62 μm | 61 μm | 65 μm | 71 μm | 64 μm |
|  | PSD | 80% or more | 80% or more | 80% or more | 80% or more | 80% or more |
|  | PC | −83.80% | −87.10% | −85.50% | −86.80% | −87.50% |
| Base Material D | V = 2500 mPs VRR = 99.5% | NG | NG | NG | NG | NG |
|  | SP | oval full cone | oval full cone | circular full cone | circular full cone | circular semi-hollow cone |
|  | SA | 50 degrees | 42 degrees | 40 degrees | 38 degrees | 55 degrees |
|  | APS | 78 μm | 88 μm | 88 μm | 86 μm | 77 μm |
|  | PSD | 80% or more | 70% or more | 70% or more | 70% or more | 70% or more |
|  | PC | −83.50% | −75.10% | −70.40% | −72.60% | −77.70% |

TABLE 10

|  |  | Nozzle a | Nozzle b | Nozzle c | Nozzle d | Nozzle e | Nozzle f |
|---|---|---|---|---|---|---|---|
|  | orifice diameter | 0.25 | 0.25 | 0.26 | 0.3 | 0.3 | 0.3 |
|  | thickness d | 0.15 | 0.25 | 0.25 | 0.13 | 0.2 | 0.3 |
|  | curved portion | no | no | yes | no | no | no |
| Base Material E1 | V = 2500 mPs VRR = 99.8% | OK | NG | OK | OK | OK | OK |
|  | SP | circular full cone | oval semi-hollow cone | circular full cone | circular full cone | circular full cone | circular full cone |
|  | SA | 42 degrees | 60 degrees | 65 degrees | 68 degrees | 52 degrees | 52 degrees |
|  | APS | 66 μm | 68 μm | 72 μm | 58 μm | 57 μm | 63 μm |
|  | PSD | 80% or more | 80% or more | 90% or more | 90% or more | 90% or more | 80% or more |
|  | PC | −87.30% | −87.10% | −91.60% | −90.50% | −91.80% | −85.40% |
| Base Material E2 | V = 2400 mPs VRR = 98.6% | OK | OK | OK | OK | OK | NG |
|  | SP | circular full cone | circular full cone | circular full cone | circular full cone | circular full cone | circular full cone |
|  | SA | 55 degrees | 48 degrees | 68 degrees | 58 degrees | 47 degrees | 35 degrees |
|  | APS | 68 μm | 71 μm | 58 μm | 56 μm | 58 μm | 75 μm |
|  | PSD | 80% or more | 80% or more | 90% or more | 90% or more | 90% or more | 80% or more |
|  | PC | −86.80% | −89.20% | −90.40% | −91.20% | −92.80% | −88.40% |
| Base Material E3 | V = 1000 mPs VRR = 100% | OK | OK | OK | OK | OK | OK |
|  | SP | circular full cone | circular full cone | circular full cone | circular full cone | circular full cone | circular full cone |
|  | SA | 58 degrees | 56 degrees | 69 degrees | 62 degrees | 52 degrees | 41 degrees |
|  | APS | 55 μm | 63 μm | 64 μm | 54 μm | 52 μm | 59 μm |
|  | PSD | 90% or more | 90% or more | 90% or more | 90% or more | 90% or more | 90% or more |
|  | PC | −90.40% | −91.30% | −92.00% | −90.80% | −91.50% | −92.60% |
| Base Material E4 | V = 1000 mPs VRR = 100% | OK | OK | NG | OK | OK | OK |
|  | SP | circular full cone | circular full cone | circular full cone | circular full cone | circular full cone | circular fill cone |
|  | SA | 69 degrees | 55 degrees | 75 degrees | 65 degrees | 52 degrees | 42 degrees |
|  | APS | 57 μm | 63 μm | 64 μm | 62 μm | 55 μm | 59 μm |
|  | PSD | 90% or more | 90% or more | 90% or more | 90% or more | 90% or more | 90% or more |
|  | PC | −90.40% | −91.30% | −92.00% | −90.80% | −92.50% | −91.60% |

|  |  | Nozzle g | Nozzle h | Nozzle i | Nozzle j | Nozzle k |
|---|---|---|---|---|---|---|
|  | orifice diameter | 0.3 | 0.4 | 0.4 | 0.45 | 0.55 |
|  | thickness d | 0.25 | 0.25 | 0.25 | 0.25 | 0.25 |
|  | curved portion | yes | no | yes | no | no |
| Base Material E1 | V = 2500 mPs VRR = 99.8% | NG | OK | OK | OK | OK |
|  | SP | circular full cone | circular full cone | circular full cone | circular full cone | circular full cone |
|  | SA | 78 degrees | 55 degrees | 42 degrees | 65 degrees | 60 degrees |
|  | APS | 64 μm | 63 μm | 67 μm | 70 μm | 65 μm |
|  | PSD | 90% or more | 80% or more | 80% or more | 80% or more | 80% or more |
|  | PC | −91.70% | −88.50% | −86.90% | (83.4%) | −82.80% |
| Base Material E2 | V = 2400 mPs VRR = 98.6% | NG | OK | OK | OK | OK |
|  | SP | circular full cone | circular full cone | circular full cone | circular full cone | circular full cone |
|  | SA | 78 degrees | 47 degrees | 48 degrees | 47 degrees | 47 degrees |
|  | APS | 66 μm | 77 μm | 75 μm | 76 μm | 73 μm |
|  | PSD | 90% or more | 80% or more | 80% or more | 80% or more | 80% or more |
|  | PC | −90.70% | −89.40% | −87.50% | (87.4%) | −88.80% |
| Base Material E3 | V = 1000 mPs VRR = 100% | OK | OK | OK | OK | OK |
|  | SP | circular full cone | circular full cone | circular full cone | circular full cone | circular full cone |
|  | SA | 68 degrees | 53 degrees | 54 degrees | 52 degrees | 62 degrees |
|  | APS | 60 μm | 68 μm | 65 μm | 63 μm | 61 μm |
|  | PSD | 90% or more | 90% or more | 90% or more | 80% or more | 80% or more |
|  | PC | −91.00% | −91.00% | −90.30% | −87.50% | −88.20% |
| Base Material E4 | V = 1000 mPs VRR = 100% | NG | OK | OK | OK | NG |
|  | SP | circular full cone | circular full cone | circular full cone | circular full cone | circular full cone |
|  | SA | 72 degrees | 55 degrees | 58 degrees | 58 degrees | 78 degrees |
|  | APS | 58 μm | 58 μm | 58 μm | 61 μm | 63 μm |
|  | PSD | 90% or more | 90% or more | 90% or more | 80% or more | 80% or more |
|  | PC | −91.10% | −91.00% | −90.30% | −88.70% | −86.90% |

[Evaluations]

If all of the aforementioned parameters including a) Viscosity (V) and Viscosity Retention Rate (VRR), b) Spray Pattern (SP), c) Spray Angle (SA), and d) Average Particle Size (APS), Particle Size Distribution (PSD) and Percentage of Counts of the particles between 10 to 100 microns (PC) are within the desired range, then the combination of the base material and the rhinal spray nozzle 10 is determined as acceptable (OK) and even one of the parameters is out of the desired range, the combination is determined as unacceptable (NG).

The base material A having very low viscosity as shown in Table 2 and the base materials B1-B2 having low viscosity retention rates as shown in Table 3 are not suitable for the rhinal spray formulation.

The base material C was prepared by adding a viscosity modification agent (sodium chloride) to have a predetermined viscosity (e.g., 2400 mPa or 1000 mPa) as shown in Table 4 so that the viscosity retention rate is high and the formulation is likely retained in the nasal cavity. Also, the base material D was prepared by applying an exogenous shear force to have a predetermined viscosity (e.g., 2500 mPa) as shown in Table 5 so that the viscosity retention rate is high and the formulation is likely retained in the nasal cavity. However, the spray pattern of the formulation containing the base materials C and D filled in the medical syringe provided with the rhinal spray nozzles 10*a*-10*k* are acceptable only for the rhinal spray nozzles 10*d* and 10*e*. Thus, the rhinal spray nozzles 10 achieve the desired spray characteristics only when it is used with the base materials C2 and has the diameter of the nozzle orifice of 0.30 mm and the thickness between 0.13 mm through 0.20 mm.

The base material E was prepared by applying an exogenous shear force to have a predetermined viscosity (e.g., 2400 mPa or 1000 mPa) as shown in Table 6 so that the viscosity retention rate is high and the formulation is likely retained in the nasal cavity. However, the rhinal spray nozzles 10*c*, 10*g* having the curved portion on the nozzle orifice 21 of the tip portion 22 failed to achieve the desired spray nozzle, thus several of the base materials E were determined as unacceptable due to failure to achieve the desired spray characteristics. When focusing on the base materials E3 and E4, all of the rhinal spray nozzles 10 achieved the desired spray characteristics when the diameter of the nozzle orifice 21 was 0.3 mm and the thickness d of the tip portion 22 was in a range between 0.13 mm and 0.20 mm.

INDUSTRIAL APPLICABILITY

As described above, the rhinal spray nozzle used for a medical syringe according to the present invention substantially improves the spray uniformity (spray pattern), the spray angle, particle size distribution (an average particle size) in spraying the pharmaceutical formulation such as an endermatic influenza vaccine comprising the gel material containing viscosity modification agent and carboxy vinyl polymer of which viscosity is modified by applying an exogenous shear force so as to improve the retention of the formulation in the nasal cavity of the patient, thereby to achieve higher pharmaceutical benefits of the formulation.

DENOTATION OF REFERENCE NUMERALS

1: medical syringe, 2: pharmaceutical formulation, 3: syringe barrel, 4: syringe body, 5: plunger rod, 5*a*: fixing member, 6: opening, 7: piston, 8: finger flange, 9: plunger end member, 10: rhinal spray nozzle, 20: nozzle body, 21: nozzle orifice, 22: tip portion, 23: inner wall, 23*a*: protrusion, 24: internal space, 25: nozzle small-diameter portion, 26: nozzle large-diameter portion, 27: nozzle shoulder, 30: packing rod, 33: outer wall, 33*a*: recess, 35: rod small-diameter portion, 36: rod large-diameter portion, 37: rod shoulder, 38, 39: groove, 40: gap, 42: nozzle chamber, 44: vortex-flow generation member, 46: curved portion, 50: protection cap.

We claim:

1. A rhinal spray nozzle for use with a medical syringe having a tip opening in fluid communication with a syringe barrel for storing a formulation, the rhinal spray nozzle comprising:

a hollow nozzle body having a tip portion defining a nozzle orifice thereon;

a solid packing rod arranged within the nozzle body; and a nozzle chamber defined between the packing rod and the nozzle body to allow a fluid communication between the tip opening and the nozzle orifice;

wherein the formulation comprises a gel material containing viscosity modification agent and carboxy vinyl polymer of which viscosity is modified by applying an exogenous shear force, and wherein the nozzle orifice has a diameter in a range between 0.25 millimeters (mm) and 0.30 mm, wherein the nozzle orifice includes a straight portion, wherein the nozzle body includes an inner wall having at least a portion formed in a cylindrical shape and the packing rod includes an outer wall at least a portion formed in a cylindrical shape having a plurality of circumferentially spaced grooves, wherein the nozzle chamber is defined between the at least portion of the inner wall of the nozzle body and the at least portion of the outer wall of the packing rod, wherein the packing rod includes a vortex-flow generation member opposed to the nozzle orifice of the nozzle body, wherein the vortex-flow generation member consists of a recess and grooves formed around and connected to the recess, and is formed so that a flow direction of the formulation from the grooves of the packing rod is offset to a central axis, thereby to generate a vortex flow of the formulation and to spray the formulation through the nozzle orifice opposed to the vortex-flow generation member, and wherein the vortex-flow generation member is located entirely within the tip portion.

2. The rhinal spray nozzle according to claim 1, wherein the formulation comprises the gel material containing an electrolyte as the viscosity modification agent which is selected from a group consisting of sodium chloride, potassium chloride, dibasic sodium phosphate hydrate, and sodium dihydrogenphosphate, of which viscosity is modified by applying an exogenous shear force.

3. The rhinal spray nozzle according to claim 1, wherein the tip portion has thickness along an injection direction of the formulation which is in a range between 0.20 mm and 0.30 mm.

4. The rhinal spray nozzle according to claim 1, wherein the at least a portion of the inner wall of the nozzle body is formed to have a cross section perpendicular to the injection direction which is continuously or step-wisely reduced towards the injection direction.

5. The rhinal spray nozzle according to claim 1, wherein the gel material has a viscosity of 2500 millipascals (mPas) or more.

6. The rhinal spray nozzle according to claim 1, wherein the gel material has a viscosity of 1000 mPas or more.

7. The rhinal spray nozzle according to claim 1, wherein the rhinal spray nozzle is configured such that a spray angle of the formulation sprayed from the nozzle orifice is in a range of 45 degrees and 60 degrees.

8. The rhinal spray nozzle according to claim 1, wherein the rhinal spray nozzle is configured such that an average particle size of formulation droplets sprayed from the nozzle orifice is in a range of 50 microns and 80 microns.

9. The rhinal spray nozzle according to claim 1, wherein the rhinal spray nozzle is configured such that counts of formulation droplets sprayed from the nozzle orifice having the particle size in a range between 10 to 100 microns are 70% or more of the total counts of the particle.

* * * * *